United States Patent
Wang et al.

(10) Patent No.: US 11,504,316 B2
(45) Date of Patent: Nov. 22, 2022

(54) PHOTOPROTECTIVE COMPOSITION BASED ON A CARBOXYLIC ACID ESTER; USE OF SAID COMPOUND FOR INCREASING THE SUN PROTECTION FACTOR

(71) Applicant: L'OREAL, Paris (FR)

(72) Inventors: Pamella Wang, Chevilly la Rue (FR); Isabelle Terrisse, Chevilly la Rue (FR)

(73) Assignee: L'OREAL, Paris (FR)

( * ) Notice: Subject to any disclaimer, the term of this patent is extended or adjusted under 35 U.S.C. 154(b) by 61 days.

(21) Appl. No.: 16/064,034

(22) PCT Filed: Dec. 15, 2016

(86) PCT No.: PCT/EP2016/081289
§ 371 (c)(1),
(2) Date: Jun. 20, 2018

(87) PCT Pub. No.: WO2017/108588
PCT Pub. Date: Jun. 29, 2017

(65) Prior Publication Data
US 2018/0369094 A1   Dec. 27, 2018

(30) Foreign Application Priority Data
Dec. 22, 2015   (FR) ..................................... 15 63156

(51) Int. Cl.
| | | |
|---|---|---|
| *A61K 8/37* | (2006.01) | |
| *A61K 8/34* | (2006.01) | |
| *A61K 8/60* | (2006.01) | |
| *A61Q 17/04* | (2006.01) | |
| *A61Q 19/00* | (2006.01) | |
| *A61Q 19/08* | (2006.01) | |

(52) U.S. Cl.
CPC ................ *A61K 8/37* (2013.01); *A61K 8/342* (2013.01); *A61K 8/604* (2013.01); *A61Q 17/04* (2013.01); *A61Q 19/004* (2013.01); *A61Q 19/08* (2013.01); *A61K 2800/43* (2013.01)

(58) Field of Classification Search
CPC .......... A61K 8/342; A61K 8/37; A61K 8/604; A61K 2800/43; A61Q 19/08; A61Q 19/004; A61Q 17/04
See application file for complete search history.

(56) References Cited

U.S. PATENT DOCUMENTS

| | | | | |
|---|---|---|---|---|
| 3,920,808 A * | 11/1975 | Fusaro | ................... | A61Q 17/04 424/46 |
| 5,763,497 A | 6/1998 | Ikeda et al. | | |
| 6,207,140 B1 * | 3/2001 | Seipel | .................... | A61K 8/062 424/400 |
| 2007/0264209 A1 * | 11/2007 | Chaudhuri | ........... | A61K 8/8129 424/59 |
| 2010/0080764 A1 * | 4/2010 | Fox | .......................... | A61K 8/68 424/60 |
| 2010/0086509 A1 * | 4/2010 | Novikov | ................ | A61K 8/732 424/70.13 |
| 2010/0247458 A1 * | 9/2010 | Kakoki | .................... | A61K 8/39 424/59 |
| 2011/0123584 A1 * | 5/2011 | Seidling | ................... | A61K 8/37 424/402 |
| 2012/0114573 A1 * | 5/2012 | Amalric | ................. | A61K 8/345 424/59 |
| 2012/0294814 A1 * | 11/2012 | Norman | ................. | A61K 8/602 424/60 |
| 2014/0127140 A1 * | 5/2014 | Ferritto | ............. | C08G 65/2639 424/43 |
| 2014/0220139 A1 * | 8/2014 | Park | ....................... | A61K 47/18 424/489 |
| 2017/0367950 A1 * | 12/2017 | Terrisse | ................... | A61K 8/37 |

FOREIGN PATENT DOCUMENTS

| | | |
|---|---|---|
| CN | 103619316 | 3/2014 |
| DE | 199 03 716 A1 | 8/2000 |
| DE | 10 2008 052520 A1 | 4/2010 |
| EP | 0 427 411 A2 | 5/1991 |
| EP | 0 881 896 A1 | 12/1998 |
| WO | WO 97/30691 A1 | 8/1997 |
| WO | WO 01/21140 A2 | 3/2001 |
| WO | WO 03/007906 A1 | 1/2003 |
| WO | WO 2015/181276 A1 | 12/2015 |

OTHER PUBLICATIONS

Latha et al Clinical Aesthetic 2013.*
Seppic, "MOV 202/01/GB", Mar. 23, 2001, XP055353407.

* cited by examiner

*Primary Examiner* — Blessing M Fubara
(74) *Attorney, Agent, or Firm* — Polsinelli PC

(57) ABSTRACT

The present invention relates to a composition, especially a cosmetic composition, characterized in that it comprises, in a cosmetically acceptable medium:

(a) at least one photoprotective system capable of screening out UV radiation;

(b) one or more carboxylic acid esters, said ester comprising at least 24 carbon atoms;

(c) at least one $C_8$-$C_{30}$alkyl(poly)glycoside.

The present invention also relates to the use of a carboxylic acid ester in a composition comprising, in a cosmetically acceptable medium, at least one photoprotective system capable of screening out UV radiation.

15 Claims, No Drawings

PHOTOPROTECTIVE COMPOSITION BASED ON A CARBOXYLIC ACID ESTER; USE OF SAID COMPOUND FOR INCREASING THE SUN PROTECTION FACTOR

CROSS REFERENCE TO RELATED APPLICATIONS

This application is the National Phase of Application No. PCT/EP2016/081289 filed Dec. 15, 2016, which claims priority to Application No. 15 63156 filed in France on Dec. 22, 2015 under 35 U.S.C. § 119. The entire contents of each application are hereby incorporated by reference.

The present invention relates to a composition, especially a cosmetic and/or dermatological composition, intended for protecting the skin and/or the hair against ultraviolet radiation, characterized in that it comprises, in a cosmetically acceptable medium, at least:
  (a) a photoprotective system capable of screening out UV radiation;
  (b) one or more carboxylic acid esters comprising at least 12 carbon atoms, said ester comprising at least 24 carbon atoms;
  (c) at least one $C_8$-$C_{30}$alkyl(poly)glycoside.

The present invention also relates to the use of a carboxylic acid ester comprising at least 12 carbon atoms, said ester comprising at least 24 carbon atoms, for increasing the sun protection factor (SPF) of a composition comprising, in a cosmetically acceptable medium, at least one photoprotective system that is capable of screening out UV radiation.

It is known that light radiation with wavelengths of between 280 nm and 400 nm permits tanning of the human epidermis and that light radiation with wavelengths between 280 and 320 nm, known as UV-B rays, harms the development of a natural tan. Exposure is also liable to induce impairment of the biomechanical properties of the epidermis, which is reflected by the appearance of wrinkles, leading to premature aging of the skin. This UV-B radiation should thus be screened out.

It is also known that UV-A rays with wavelengths of between 320 and 400 nm penetrate more deeply into the skin than UV-B rays. UV-A rays cause immediate and persistent browning of the skin. Under normal conditions, daily exposure to UVA rays, even of short duration, can result in damage to the collagen fibers and the elastin, which is reflected by a modification to the microrelief of the skin, the appearance of wrinkles and uneven pigmentation (liver spots, non-uniformity of the complexion). It is therefore desirable also to screen out UV-A radiation.

Many cosmetic compositions intended to limit darkening of the skin, and to improve the color and uniformity of the complexion have been proposed to date. It is well known in the field of suntan products that such compositions can be obtained by using UV-screening agents, and in particular UVB-screening agents. Some compositions may also contain UVA-screening agents. This screening system must cover UVB protection for the purpose of limiting and controlling the neosynthesis of melanin promoting overall pigmentation, but must also cover UVA protection in order to limit and control the oxidation of the already existing melanin resulting in darkening of the skin.

Advantageously, this improvement is particularly desired on skin that is already pigmented, for the purpose of not increasing either the pigmentary melanin load or the structure of the melanin already present within the skin.

Thus, there is still a great need to find antisun products with a sufficiently high protection factor. High protection factors may be achieved by incorporating more screening agents at high concentrations. This is not always achievable despite the addition of large amounts of screening agents. Furthermore, such amounts may lead to drawbacks as regards the comfort (tacky or coarse effect and/or greasy effect). Specifically, sunscreens, in particular lipophilic sunscreens, provide an undesirable greasy effect.

EP 0 427 411 describes photoprotective topical compositions comprising UV-screening agents and a fatty acid ester.

EP 0 881 896 discloses methods for the cosmetic treatment of skin complaints, comprising the application to the skin of a salicylic acid ester and a retinoid ester.

WO 03/007 906 describes compositions comprising photostable organic UV-screening agents with antioxidant properties.

DE 10 2008 052 520, U.S. Pat. No. 5,763,497 and WO 2015/181 276 disclose compositions comprising esters, especially fatty acid esters.

However, none of these documents makes it possible to obtain a stable composition with a high protection factor and good cosmetic properties.

There is still a need to find compositions which are sufficiently effective in photoprotection, which have good stability and also good cosmetic properties such as easy spreading, a non-greasy feel and good glidance, and which do not have the drawbacks presented above.

Now, after considerable research conducted in the field of photoprotection mentioned above, the Applicant has discovered, surprisingly, that the addition of a particular carboxylic acid ester to a composition containing at least one system for screening out UV radiation makes it possible to increase its photoprotection efficacy and in particular its sun protection factor.

Furthermore, the compositions according to the invention make it possible to reduce the greasy effect due to UV-screening agents, in particular lipophilic screening agents.

This discovery forms the basis of the present invention.

Thus, novel compositions are described, especially cosmetic compositions, which are intended in particular for protecting the skin and/or the hair against ultraviolet radiation, characterized in that they comprise, in a medium, especially a cosmetically acceptable medium, at least:
  (a) a photoprotective system capable of screening out UV radiation;
  (b) one or more carboxylic acid esters comprising at least 12 carbon atoms, said ester comprising at least 24 carbon atoms.

According to a first aspect, the invention relates to a composition, especially a cosmetic composition, characterized in that it comprises, in a medium, especially a cosmetically acceptable medium:
  (a) at least one photoprotective system capable of screening out UV radiation;
  (b) at least one carboxylic acid ester comprising at least 12 carbon atoms, said ester comprising at least 24 carbon atoms;
  (c) at least one $C_8$-$C_{30}$alkyl(poly)glycoside.

The invention also describes a composition, especially a cosmetic composition, characterized in that it comprises, in a medium, especially a cosmetically acceptable medium:
  (a) at least one photoprotective system capable of screening out UV radiation;

(b) from 0.5% to 5% by weight, relative to the total weight of the composition, of at least one carboxylic acid ester chosen from those corresponding to formula (I) below:

R—COO—R'  (I)

in which:

R and R' are identical and represent a $C_{14}$-$C_{24}$ alkyl group, said composition also comprising at least one nonionic emulsifier.

According to the invention, the term "photoprotective system capable of screening out UV radiation" is generally intended to denote any compound or any combination of compounds which, via mechanisms that are known per se for the absorption and/or reflection and/or scattering of UV-A and/or UV-B radiation, can prevent, or at least limit, the contact of said radiation with a surface (skin, hair) onto which this or these compounds have been applied. In other words, these compounds may be UV-absorbing photoprotective organic screening agents or UV-scattering and/or UV-reflecting mineral pigments, and also mixtures thereof.

The term "cosmetically acceptable" means compatible with the skin and/or its integuments, having a pleasant color, odor and feel and not causing any unacceptable discomfort (stinging, tautness or redness) liable to discourage the consumer from using this composition.

Yet another subject of the present invention lies in the use of at least one carboxylic acid ester defined below in a composition comprising, in a cosmetically acceptable medium, at least one photoprotective system capable of screening out UV radiation, for the purpose of increasing the sun protection factor (SPF).

In other words, the present invention also relates to the use of at least one carboxylic acid ester as defined below for increasing the sun protection factor (SPF) of a composition comprising, in a cosmetically acceptable medium, at least one photoprotective system capable of screening out UV radiation.

The invention also relates to the use of at least one carboxylic acid ester as defined below for increasing the sun protection factor (SPF) of a composition comprising, in a cosmetically acceptable medium, at least one photoprotective system capable of screening out UV radiation and at least one $C_8$-$C_{30}$alkyl(poly)glycoside.

Another subject of the present invention consists of a cosmetic process for caring for and/or making up a keratin material, comprising the application, to the surface of said keratin material, of a composition according to the invention as defined above.

The invention also relates to a cosmetic process for limiting the darkening of the skin and/or improving the color and/or uniformity of the complexion, comprising the application, to the surface of the keratin material, of a composition as defined previously.

The invention also relates to a cosmetic process for preventing and/or treating the signs of aging of a keratin material, comprising the application, to the surface of the keratin material, of a composition as defined previously.

Definitions

The following definitions are used in the present text.

The term "human keratin materials" means the skin (of the body, face and around the eyes), hair, lips or mucous membranes.

The term "physiologically acceptable" means compatible with the skin and/or its integuments, which has a pleasant color, odor and feel, and which does not cause any unacceptable discomfort (stinging, tautness or redness) liable to discourage the consumer from using this composition.

The term "cosmetically acceptable medium" means a medium that is compatible with human keratin materials, in particular with the skin, the hair, the lips and mucous membranes.

According to the invention, the term "preventing" or "prevention" means reducing the risk of occurrence or slowing down the occurrence of a given phenomenon, namely, according to the present invention, the signs of aging of a keratin material.

The term "UV-screening agent" refers to a molecule that is capable of screening out UV radiation between 290 and 400 nm.

The term "mean elementary size" means the size of non-aggregated particles.

Other characteristics, aspects and advantages of the present invention will emerge on reading the detailed description that follows.

Carboxylic Acid Esters

The carboxylic acid esters comprising at least 24 carbon atoms are in particular esters comprising two or three $C_{12}$-$C_{30}$ fatty chains.

The total number of carbon atoms in the ester ranges from 30 to 100 and preferably from 40 to 80.

They are preferably solid at a temperature of less than or equal to about 30° C.

The carboxylic acid esters according to the invention are especially those corresponding to formula (I) below:

R—COO—R'  (I)

in which:

R and R', which may be identical or different, denote a saturated or unsaturated, linear or branched hydrocarbon-based group comprising from 12 to 30 carbon atoms and preferably from 14 to 24 carbon atoms.

Preferably, R and R', which may be identical or different, denote a saturated, linear hydrocarbon-based group comprising from 12 to 30 carbon atoms and preferably from 14 to 24 carbon atoms.

The radicals R and R' may be hydroxylated. R and R' are chosen such that the compound of formula (I) is solid at a temperature of lower than or equal to approximately 30° C. In particular, R and R' denote a $C_{14}$-$C_{24}$ alkyl group such as behenyl, stearyl or arachidyl. Preferably, R and R' are identical and denote a $C_{14}$-$C_{24}$ alkyl group such as behenyl, stearyl or arachidyl.

Preferred compounds of formula (I) are, for example, behenyl behenate, stearyl stearate, arachidyl arachidate and more particularly behenyl behenate.

The carboxylic acid esters according to the invention are generally present in the compositions according to the invention in concentrations ranging from 0.01% to 10% by weight, preferably from 0.1% to 10% by weight, more preferentially from 0.5% to 5% by weight and even more preferentially from 1% to 3% by weight relative to the total weight of the composition.

Photoprotective System

According to the invention, the photoprotective system may be formed from one or more hydrophilic, lipophilic or insoluble organic screening agents and/or one or more mineral screening agents such as mineral pigments. It will preferentially be formed from at least one hydrophilic, lipophilic or insoluble organic UV-screening agent.

The organic UV-screening agents are especially chosen from cinnamic derivatives; anthranilates; salicylic derivatives; dibenzoylmethane derivatives; camphor derivatives;

benzophenone derivatives; β,β-diphenylacrylate derivatives; triazine derivatives; benzotriazole derivatives; benzalmalonate derivatives, especially those mentioned in U.S. Pat. No. 5,624,663; benzimidazole derivatives; imidazolines; bis-benzazolyl derivatives such as those described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. Nos. 5,237,071, 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers such as those described in patent application DE 1 9855 649; 4,4-diarylbutadienes as described in patent applications EP 0 967 200, DE 19 746 654, DE 19 755 649, EP-A-1 008 586, EP 1 133 980 and EP 1 133 981; merocyanine derivatives such as those described in patent applications WO 04/006 878, WO 05/058 269 and WO 06/032 741, and mixtures thereof.

As examples of additional organic photoprotective agents, mention may be made of those denoted hereinbelow under their INCI name:

Cinnamic Derivatives:
Ethylhexyl Methoxycinnamate, sold especially under the trade name Parsol MCX by DSM Nutritional Products,
Isopropyl methoxycinnamate,
Isoamyl methoxycinnamate sold under the trade name Neo Heliopan E 1000 by Symrise,
DEA methoxycinnamate,
Diisopropyl methylcinnamate,
Glyceryl ethylhexanoate dimethoxycinnamate.
Dibenzoylmethane Derivatives:
Butylmethoxydibenzoylmethane sold especially under the trade name Parsol 1789
by DSM,
Isopropyldibenzoylmethane.
Para-Aminobenzoic Acid Derivatives:
PABA,
Ethyl PABA,
Ethyl dihydroxypropyl PABA,
Ethylhexyl dimethyl PABA sold especially under the name Escalol 507 by ISP,
Glyceryl PABA,
PEG-25 PABA sold under the name Uvinul P25 by BASF.
Salicylic Derivatives:
Homosalate sold under the name Eusolex HMS by Rona/EM Industries,
Ethylhexyl salicylate sold under the name Neo Heliopan OS by Symrise,
Dipropylene glycol salicylate sold under the name Dipsal by Scher,
TEA salicylate sold under the name Neo Heliopan TS by Symrise.
B3,1-Diphenylacrylate Derivatives:
Octocrylene sold in particular under the trade name Uvinul N539 by BASF,
Etocrylene sold especially under the trade name Uvinul N35 by BASF.
Benzophenone Derivatives:
Benzophenone-1, sold under the trade name Uvinul 400 by BASF,
Benzophenone-2, sold under the trade name Uvinul D50 by BASF,
Benzophenone-3 or oxybenzone sold under the trade name Uvinul M40 by BASF,
Benzophenone-4 sold under the trade name Uvinul MS40 by BASF,
Benzophenone-5,
Benzophenone-6, sold under the trade name Helisorb 11 by Norquay,
Benzophenone-8, sold under the trade name Spectra-Sorb UV-24 by American
Cyanamid,
Benzophenone-9, sold under the trade name Uvinul DS-49 by BASF,
Benzophenone-12,
n-Hexyl 2-(4-diethylamino-2-hydroxybenzoyl)benzoate sold under the trade name
Uvinul A+ or as a mixture with octyl methoxycinnamate under the trade name
Uvinul A+B by the company BASF.
Benzylidenecamphor Derivatives:
3-Benzylidenecamphor manufactured under the name Mexoryl SD by Chimex,
4-Methylbenzylidenecamphor sold under the name Eusolex 6300 by Merck,
Benzylidenecamphorsulfonic acid, manufactured under the name Mexoryl SL by Chimex,
Camphor benzalkonium methosulfate manufactured under the name Mexoryl SO by Chimex,
Terephthalylidenedicamphorsulfonic acid manufactured under the name Mexoryl SX by Chimex,
Polyacrylamidomethylbenzylidenecamphor manufactured under the name Mexoryl SW by Chimex.
Phenylbenzimidazole Derivatives:
Phenylbenzimidazolesulfonic acid sold especially under the trade name Eusolex 232 by Merck,
Disodium phenyl dibenzimidazole tetrasulfonate sold under the trade name Neo
Heliopan AP by Symrise.
Phenylbenzotriazole Derivatives:
Drometrizole trisiloxane sold under the name Silatrizole by Rhodia Chimie,
Methylenebis(benzotriazolyl)tetramethylbutylphenol
sold in solid form under the trade name Mixxim BB/100 by Fairmount Chemical, or in micronized form as an aqueous dispersion under the trade name Tinosorb M by Ciba Specialty Chemicals.
Triazine Derivatives:
Bis(ethylhexyloxyphenol)methoxyphenyltriazine sold under the trade name Tinosorb S by Ciba Geigy,
Ethylhexyl triazone sold especially under the trade name Uvinul T150 by BASF,
Diethylhexyl butamidotriazone sold under the trade name Uvasorb HEB by Sigma 3V,
2,4,6-tris(dineopentyl 4'-aminobenzalmalonate)-s-triazine,
2,4,6-tris(diisobutyl 4'-aminobenzalmalonate)-s-triazine,
2,4-bis(dineopentyl 4'-aminobenzalmalonate)-6-(n-butyl 4'-aminobenzoate)-s-triazine,
the symmetrical triazine screening agents described in U.S. Pat. No. 6,225,467, patent application WO 2004/085 412 (see compounds 6 and 9) or the document Symmetrical Triazine Derivatives IP.COM Journal, IP.COM INC West Henrietta, N.Y., US (Sep. 20, 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in patent applications WO 06/035 000, WO 06/034 982, WO 06/034 991, WO 06/035 007, WO 2006/034 992 and WO 2006/034 985.

Anthranilic Derivatives:
Menthyl anthranilate sold under the trade name Neo Heliopan MA by Symrise,
Imidazoline derivatives:
Ethylhexyl dimethoxybenzylidene dioxoimidazoline propionate,
Benzalmalonate Derivatives:
Polyorganosiloxane bearing benzalmalonate functions, for instance Polysilicone-15, sold under the trade name Parsol SLX by DSM Nutritional Products.
4,4-Diarylbutadiene Derivatives:
1,1-Dicarboxy(2,2'-dimethylpropyl)-4,4-diphenylbutadiene,
Benzoxazole Derivatives:
2,4-Bis[5-1 (dimethylpropyl)benzoxazol-2-yl-(4-phenyl)imino]-6-(2-ethylhexyl)imino-1,3,5-triazine, sold under the name Uvasorb K2A by Sigma 3V, and mixtures thereof.
The preferential organic screening agents are chosen from:
Ethylhexyl methoxycinnamate,
Ethylhexyl salicylate,
Homosalate,
Butylmethoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Bis(ethylhexyloxyphenol)methoxyphenyltriazine,
Ethylhexyl triazone,
Diethylhexyl butamidotriazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane,
Polysilicone-15,
1,1-Dicarboxy(2,2'-dimethylpropyl)-4,4-diphenylbutadiene;
2,4-Bis[5-(1-dimethylpropyl)benzoxazol-2-yl-(4-phenyl)imino]-6-(2-ethylhexyl)imino-1,3,5-triazine,
and mixtures thereof.
The mineral UV-screening agents used in accordance with the present invention are metal oxide pigments. More preferentially, the mineral UV-screening agents of the invention are metal oxide particles with a mean elementary particle size of less than or equal to 500 nm, more preferentially between 5 nm and 500 nm, even more preferentially between 10 nm and 100 nm and preferentially between 15 nm and 50 nm.
They may be chosen in particular from titanium oxide, zinc oxide, iron oxide, zirconium oxide and cerium oxide, or mixtures thereof.
Such coated or uncoated metal oxide pigments are described in particular in patent application EP-A-0 518 773. Commercial pigments that may be mentioned include the products sold by the companies Kemira, Tayca, Merck and Degussa.
The metal oxide pigments may be coated or uncoated.
The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.
The coated pigments are more particularly titanium oxides that have been coated:
with silica, such as the product Sunveil from the company Ikeda,
with silica and iron oxide, such as the product Sunveil F from Ikeda,
with silica and alumina, such as the products Microtitanium Dioxide MT 500 SA and Microtitanium Dioxide MT 100 SA from the company Tayca and Tioveil from the company Tioxide,
with alumina, such as the products Tipaque TTO-55 (B) and Tipaque TTO-55 (A) from the company Ishihara and UVT 14/4 from the company Kemira,
with alumina and aluminum stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck,
with silica, alumina and alginic acid, such as the product MT-100 AQ from the company Tayca,
with alumina and aluminum laurate, such as the product Microtitanium Dioxide MT 100 S from the company Tayca,
with iron oxide and iron stearate, such as the product Microtitanium Dioxide MT 100 F from the company Tayca,
with zinc oxide and zinc stearate, such as the product BR 351 from the company Tayca,
with silica and alumina and treated with a silicone, such as the products Microtitanium Dioxide MT 600 SAS, Microtitanium Dioxide MT 500 SAS or Microtitanium Dioxide MT 100 SAS from the company Tayca,
with silica, alumina and aluminum stearate and treated with a silicone, such as the product STT-30-DS from the company Titan Kogyo,
with silica and treated with a silicone, such as the product UV-Titan X 195 from the company Kemira,
with alumina and treated with a silicone, such as the products Tipaque TTO-55 (S) from the company Ishihara or UV Titan M 262 from the company Kemira,
with triethanolamine, such as the product STT-65-S from the company Titan Kogyo,
with stearic acid, such as the product Tipaque TTO-55 (C) from the company Ishihara,
with sodium hexametaphosphate, such as the product Microtitanium Dioxide MT 150 W from the company Tayca,
$TiO_2$ treated with octyltrimethylsilane, sold under the trade name T 805 by the company Degussa Silices,
$TiO_2$ treated with a polydimethylsiloxane, sold under the trade name 70250 Cardre UF TiO2SI3 by the company Cardre,
anatase/rutile $TiO_2$ treated with a polydimethylhydrogenosiloxane, sold under the trade name Microtitanium Dioxide USP Grade Hydrophobic by the company Color Techniques.
The uncoated titanium oxide pigments are sold, for example, by the company Tayca under the trade names Microtitanium Dioxide MT 500 B or Microtitanium Dioxide MT 600 B, by the company Degussa under the name P 25, by the company Wackherr under the name Transparent Titanium Oxide PW, by the company Miyoshi Kasei under the name UFTR, by the company Tomen under the name ITS and by the company Tioxide under the name Tioveil AQ.

The uncoated zinc oxide pigments are, for example:
those sold under the name Z-Cote by the company Sunsmart;
those sold under the name Nanox by the company Elementis;
those sold under the name Nanogard WCD 2025 by the company Nanophase Technologies.

The coated zinc oxide pigments are, for example:
those sold under the name Zinc Oxide CS-5 by the company Toshibi (ZnO coated with polymethylhydrosiloxane);
those sold under the name Nanogard Zinc Oxide FN by the company Nanophase Technologies (as a 40% dispersion in Finsolv TN, $C_{12}$-$C_{15}$ alkyl benzoate);
those sold under the name Daitopersion ZN-30 and Daitopersion ZN-50 by the company Daito (dispersions in cyclopolymethylsiloxane/oxyethylenated polydimethylsiloxane, containing 30% or 50% of nano zinc oxides coated with silica and polymethylhydrosiloxane);
those sold under the name NFD Ultrafine ZnO by the company Daikin (ZnO coated with perfluoroalkyl phosphate and copolymer based on perfluoroalkylethyl as a dispersion in cyclopentasiloxane);
those sold under the name SPD-Z1 by the company Shin-Etsu (ZnO coated with silicone-grafted acrylic polymer, dispersed in cyclodimethylsiloxane);
those sold under the name Escalol Z100 by the company ISP (alumina-treated ZnO dispersed in an ethylhexyl methoxycinnamate/PVP-hexadecene copolymer/methicone mixture);
those sold under the name Fuji ZnO-SMS-10 by the company Fuji Pigment (ZnO coated with silica and polymethylsilsesquioxane);
those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments may, for example, be those sold under the name Colloidal Cerium Oxide by the company Rhone-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

According to the invention, coated or uncoated titanium oxide pigments are particularly preferred.

The photoprotective system according to the invention is preferably present in the compositions according to the invention in a content ranging from 0.1% to 40% by weight and in particular from 5% to 25% by weight relative to the total weight of the composition.

$C_8$-$C_{30}$Alkyl(Poly)Glycosides

The composition according to the invention also comprises at least one $C_8$-$C_{30}$alkyl(poly)glycoside.

These surfactants may more particularly be represented by the following general formula:

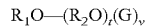

$$R_1O-(R_2O)_t(G)_v$$

in which $R_1$ represents a linear or branched alkyl and/or alkenyl radical comprising approximately from 8 to 30 carbon atoms, an alkylphenyl radical, the linear or branched alkyl radical of which comprises from 8 to 24 carbon atoms, $R_2$ represents an alkylene radical comprising approximately from 2 to 4 carbon atoms, G represents a sugar unit comprising from 5 to 6 carbon atoms, t denotes a value ranging from 0 to 10, preferably from 0 to 4, preferably from 0 to 3, and v denotes a value ranging from 1 to 15, preferably from 1 to 4.

It should also be noted that each unit of the polysaccharide part of the alkylpolyglycoside may be in a or 13 isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

According to a particular embodiment, the alkyl(poly) glycosides are compounds having the formula described above in which $R_1$ more particularly denotes a saturated or unsaturated and linear or branched alkyl radical comprising from 12 to 24 carbon atoms, t denotes a value ranging from 0 to 3 and even more particularly equal to 0, and G may denote glucose, fructose, galactose, maltose, maltotriose, lactose, cellobiose, mannose, ribose, dextran, talose, allose, xylose, levoglucan, cellulose or starch, preferably glucose. The degree of polymerization, i.e. the value of v in the above formula, may range from 1 to 5, preferably from 1 to 4. The average degree of polymerization is more particularly between 1 and 2.5, preferably from 1.05 to 2.5 and more preferentially from 1.1 to 2.

The glucoside bonds between the sugar units are of 1-6 or 1-4 type and preferably of 1-4 type.

Use may preferably be made of cocoyl(poly)glucoside (for example MONTANOV 82® and MONTANOV S®), arachidyl(poly)glucoside (for example MONTANOV 202®), myristyl(poly)glucoside (for example MONTANOV 14®), cetylstearyl(poly)glucoside (for example MONTANOV 68®), $C_{12}$-$C_{20}$ alkyl(poly)glucosides (for example MONTANOV L®), isostearyl(poly)glucoside (for example Montanov WO 18®), or octyldodecyl(poly)xyloside (for example FLUIDANOV 20X®).

According to a particular embodiment, the composition according to the invention also comprises a C8-40 fatty alcohol.

Thus, according to a preferred embodiment, the $C_8$-$C_{30}$alkyl(poly)glycoside is in mixture with at least one fatty alcohol.

The term "fatty alcohol" means a long-chain aliphatic alcohol comprising from 8 to carbon atoms and comprising at least one hydroxyl group OH.

Preferably, the fatty alcohols have the structure R—OH with R denoting a linear alkyl group, optionally substituted with one or more hydroxyl groups, comprising from 8 to 40, better still from 10 to 30, or even from 12 to 24 and even better still from 14 to 22 carbon atoms.

The fatty alcohols that can be used may be chosen, alone as a mixture, from lauryl alcohol (1-dodecanol), myristyl alcohol (1-tetradecanol), cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol) and myricyl alcohol (1-triacontanol).

Preferentially, the fatty alcohol is chosen from cetyl alcohol, stearyl alcohol, arachidyl alcohol and behenyl alcohol, and mixtures thereof, and even more preferentially from arachidyl alcohol and behenyl alcohol, and mixtures thereof.

Thus, use may be made especially of decyl glucoside and lauryl glucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of the mixture of arachidyl and behenyl alcohols and of arachidyl glucoside, sold under the name Montanov 202 by the company SEPPIC.

According to one particular embodiment of the invention, the mixture of the alkylpolyglucoside as defined above with the corresponding fatty alcohol may be in the form of a self-emulsifying composition, for example as described in WO-A-92/06778.

More preferentially, use will be made of arachidyl(poly) glucoside such as the commercial product Montanov 202® from SEPPIC.

In particular, the $C_8$-$C_{30}$alkyl(poly)glycoside(s) are present in concentrations ranging from 0.01% to 10% by weight, preferably from 0.1% to 6% by weight and more preferentially from 0.5% to 4% by weight relative to the total weight of the composition.

Preferably, the fatty alcohol(s) are present in concentrations ranging from 0.01% to 15% by weight, preferably from 0.1% to 10% by weight and more preferentially from 0.5% to 5% by weight relative to the total weight of the composition.

The compositions in accordance with the present invention may also comprise standard cosmetic adjuvants chosen especially from fatty substances, organic solvents, ionic or nonionic, hydrophilic or lipophilic thickeners, softeners, humectants, opacifiers, stabilizers, cosmetic or dermatological active agents, emollients, silicones, antifoams, preserving agents, anionic, cationic, nonionic, zwitterionic or amphoteric surfactants, fillers, polymers, propellants, basifying or acidifying agents or any other ingredient commonly used in the cosmetic and/or dermatological field.

The fatty substances may be formed from an oil or a wax other than the apolar waxes as defined above, or mixtures thereof. The term "oil" means a compound that is liquid at room temperature. The term "wax" means a compound that is solid or substantially solid at room temperature and whose melting point is generally greater than 35° C.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters, for instance the $C_{12}$-$C_{15}$ alkyl benzoate sold under the trade name Finsolv TN or Witconol TN by the company Witco, 2-ethylphenyl benzoate, for instance the commercial product sold under the name X-Tend 226® by the company ISP, octyl palmitate, isopropyl lanolate and triglycerides, including capric/caprylic acid triglycerides, and dicaprylyl carbonate sold under the name Cetiol CC by the company Cognis, oxyethylenated or oxypropylenated fatty esters and ethers; silicone oils (cyclomethicone and polydimethylsiloxanes, or PDMS) or fluoro oils, polyalkylenes, and trialkyl trimellitates such as tridecyl trimellitate.

Waxy compounds that may be mentioned include carnauba wax, beeswax, hydrogenated castor oil, polyethylene waxes and polymethylene waxes, for instance the product sold under the name Cirebelle 303 by the company Sasol.

Mention may be made, among organic solvents, of lower alcohols and polyols. These polyols may be chosen from glycols and glycol ethers, for instance ethylene glycol, propylene glycol, 1,3-propanediol, butylene glycol, pentylene glycol, dipropylene glycol or diethylene glycol. The alcohols are especially C1-C4 monoalcohols, for instance ethanol, propanol or isopropanol.

The organic solvents, when they are present in the composition of the invention, preferably represent from 0.01% to 50% by weight and more preferentially from 1% to 20% by weight, relative to the total weight of the composition.

Hydrophilic thickeners that may be mentioned include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers sold under the names Sepigel 305 (CTFA name: polyacrylamide/$C_{13-14}$ isoparaffin/Laureth 7) or Simulgel 600 (CTFA name: acrylamide/sodium acryloyldi methyltau rate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Clariant under the trade name Hostacerin AMPS (CTFA name: ammonium polyacryloyldimethyl taurate or Simulgel 800 sold by the company SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethylcellulose; polysaccharides and especially gums such as xanthan gum; water-soluble or water-dispersible silicone derivatives, for instance acrylic silicones, polyether silicones and cationic silicones, and mixtures thereof.

Lipophilic thickeners that may be mentioned include synthetic polymers such as poly($C_{10}$-$C_{30}$alkyl acrylates) sold under the name Intelimer IPA 13-1 and Intelimer IPA 13-6 by the company Landec, or modified clays such as hectorite and derivatives thereof, for instance the products sold under the name Bentone.

Needless to say, those skilled in the art will take care to select the abovementioned optional additional compound(s) and/or the amounts thereof so that the advantageous properties intrinsically associated with the compositions in accordance with the invention are not, or not substantially, adversely affected by the envisaged addition(s).

The composition according to the invention may be aqueous or anhydrous.

The mass content of water in the composition is preferably greater than or equal to 10%, advantageously 30%, preferentially 40% or even 50%, relative to the total weight of the composition.

The term "anhydrous composition" means a composition containing less than 5% by weight of water relative to the total weight of the composition, or even less than 2% by weight of water, and especially free of water, the water not being added during the preparation of the composition but corresponding to the residual water provided by the mixed ingredients.

The compositions according to the invention comprise a fatty phase which comprises at least said carboxylic acid ester according to the invention.

For the purposes of the invention, the fatty phase includes any liquid fatty substance, generally oils (also known as liquid fatty phase or oily phase), or solid fatty substance like waxes.

For the purposes of the invention, a liquid fatty phase comprises at least one oil. The term "oil" means any fatty substance that is in liquid form at room temperature and atmospheric pressure.

An oily phase that is suitable for preparing the cosmetic compositions according to the invention may comprise hydrocarbon-based oils, silicone oils, fluoro oils or non-fluoro oils, or mixtures thereof.

The oils may be volatile or nonvolatile.

They may be of animal, plant, mineral or synthetic origin. According to one implementation variant, oils of plant origin are preferred.

For the purposes of the present invention, the term "non-volatile oil" means an oil with a vapor pressure of less than 0.13 Pa.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a non-zero vapor pressure, at room temperature and atmospheric pressure, especially having a vapor pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched $C_8$-$C_{16}$ alkanes, for instance $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, for instance isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, mixtures of n-undecane ($C_{11}$) and of n-tridecane ($C_{13}$) obtained in Examples 1 and 2 of patent application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane and dodecamethylcyclohexasiloxane.

Nonvolatile Oils

The nonvolatile oils may be chosen especially from nonvolatile hydrocarbon-based, fluoro and/or silicone oils.

Nonvolatile hydrocarbon-based oils that may especially be mentioned include:

hydrocarbon-based oils of animal origin, hydrocarbon-based oils of plant origin, synthetic ethers containing from 10 to 40 carbon atoms, such as dicaprylyl ether, synthetic esters, such as the oils of formula $R_1COOR_2$, in which $R_1$ represents a linear or branched fatty acid residue comprising from 1 to 40 carbon atoms and $R_2$ represents a hydrocarbon-based chain, which is in particular branched, containing from 1 to 40 carbon atoms, on condition that $R_1+R_2 \geq 10$. The esters may be chosen especially from alcohol and fatty acid esters, for instance cetostearyl octanoate, isopropyl alcohol esters, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate, polyol esters and pentaerythritol esters, such as dipentaerythrityl tetrahydroxystearate/tetraisostearate, fatty alcohols that are liquid at room temperature, with a branched and/or unsaturated carbon-based chain containing from 12 to 26 carbon atoms, for instance 2-octyldodecanol, isostearyl alcohol and oleyl alcohol, $C_{12}$-$C_{22}$ higher fatty acids, such as oleic acid, linoleic acid, linolenic acid, and mixtures thereof, nonphenyl silicone oils, for instance caprylyl methicone, and phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicone with a viscosity of less than or equal to 100 cSt, and trimethylpentaphenyltrisiloxane, and mixtures thereof; and also mixtures of these various oils.

Preferably, a composition according to the invention comprises volatile and/or non-volatile silicone oils.

A composition according to the invention may comprise from 5% to 95% by weight, better still from 5% to 40% by weight and preferably from 7% to 35% by weight of oil(s) relative to the total weight of said composition.

Waxes

For the purposes of the present invention, the term "wax" means a lipophilic fatty compound that is solid at room temperature (25° C.), with a reversible solid/liquid change of state, having a melting point of greater than 30° C. which may be up to 200° C., a hardness of greater than 0.5 MPa, and having anisotropic crystal organization in the solid state. By bringing the wax to its melting point, it is possible to make it miscible with oils and to form a microscopically homogeneous mixture, but on returning the temperature of the mixture to room temperature, recrystallization of the wax in the oils of the mixture is obtained.

The waxes that may be used in the invention are compounds that are solid at room temperature, which are intended to structure the composition in particular in stick form; they may be hydrocarbon-based, fluoro and/or silicone and may be of plant, mineral, animal and/or synthetic origin. In particular, they have a melting point of greater than 40° C. and better still greater than 45° C.

As waxes that may be used in the invention, mention may be made of those generally used in cosmetics: they are especially of natural origin, such as beeswaxes, carnauba wax, candelilla wax, ouricury wax, Japan wax, cork fiber wax or sugarcane wax, rice wax, montan wax, paraffin waxes, lignite wax or microcrystalline wax, ceresin or ozokerite, hydrogenated waxes such as jojoba oil; synthetic waxes such as polyethylene waxes derived from the polymerization or copolymerization of ethylene and Fischer-Tropsch waxes, or alternatively fatty acid esters such as octacosanyl stearate, glycerides that are concrete at 40° C. and better still at 45° C., silicone waxes such as alkyl or alkoxy dimethicones with an alkyl or alkoxy chain of 10 to 45 carbon atoms, poly(di)methylsiloxane esters that are solid at 40° C., the ester chain of which comprises at least 10 carbon atoms; and mixtures thereof.

As a guide, a composition according to the invention may comprise from 0.01% to 50%, preferably from 2% to 40% and better still from 5% to 30% by weight of wax(es), relative to the total weight of the composition. In the case of emulsions, the proportion of fatty phase will be chosen according to the sense of the emulsion.

The fatty phase may thus be present in the composition in an amount ranging from 1% to 90%, better still ranging from 5% to 80% and even better still from 10% to 70% by weight relative to the total weight of the composition.

The compositions according to the invention may be prepared according to the techniques that are well known to those skilled in the art. They may in particular be in the form of a simple or complex emulsion (O/W, W/O, O/W/O or W/O/W) such as a cream or a milk; in the form of a lotion.

Preferably, the compositions according to the invention are in the form of an oil-in-water or water-in-oil emulsion.

The emulsions generally contain at least one emulsifier chosen from amphoteric, anionic, cationic or nonionic emulsifiers, used alone or as a mixture. The emulsifiers are chosen in an appropriate manner according to the emulsion to be obtained (W/O or O/W emulsion). The emulsions may also contain stabilizers of other types, for instance fillers, or gelling or thickening polymers.

The emulsifier surfactants are advantageously different from the $C_8$-$C_{30}$alkyl(poly)glycosides under consideration according to the invention.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as lauryl methicone copolyol sold under the name Dow Corning 5200 Formulation Aid by the company Dow Corning; cetyl dimethicone copolyol, such as the product sold under the name Abil EM 90R by the company Goldschmidt, and the mixture of cetyl dimethicone copolyol, of polyglyceryl isostearate (4 mol) and of hexyl laurate, sold under the name Abil WE 09 by the company Goldschmidt. One or more coemulsifiers, which may be chosen advantageously from the group comprising polyol alkyl esters, may also be added thereto. Mention may also be made of OCTYLDODECANOL (AND) OCTYLDODECYLXYLOSIDE (Fluidanov 20X), polyglyceryl-2 dipolyhydroxystearate (Dehymuls PGPH), polyglyceryl-3 ricinoleate (Akoline PGPR) and polyglyceryl-3 diisostearate (Lameform TG1).

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may especially be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters such as the PEG-100 stearate/glyceryl stearate mixture sold, for example, by the company ICI under the name Arlacel 165; oxyalkylenated (oxyethylenated and/or oxypropylenated) fatty alkyl ethers; sugar esters such as sucrose stearate; fatty alkyl ethers of sugar. Mention may also be made of lecithins and derivatives (for example Biophilic), sugar esters and sodium stearoyl lactylate.

Among the other emulsion stabilizers that will be used more particularly are isophthalic acid or sulfoisophthalic acid polymers, and in particular phthalate/sulfoisophthalate/glycol copolymers, for example the diethylene glycol/phthalate/isophthalate/1,4-cyclohexanedimethanol copolymer (INCI name: Polyester-5) sold under the name Eastman AQ Polymer (AQ35S, AQ38S, AQ55S and AQ48 Ultra) by the company Eastman Chemical.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, in particular cosmetic treatments, for facial or bodily skin, the lips and the hair, including the scalp, in particular for protecting and/or caring for the skin and/or the lips, and/or for making up the skin and/or the lips.

Another subject of the present invention is constituted of the use of the compositions according to the invention as defined above for the manufacture of products for the cosmetic treatment of the skin, the lips, the nails, the hair, the eyelashes, the eyebrows and/or the scalp, especially care products, antisun products and makeup products, especially for the skin, the lips and the nails.

The cosmetic compositions according to the invention may be used, for example, as makeup products.

The cosmetic compositions according to the invention may be used, for example, as care products and/or antisun products for the face and/or body, with a liquid to semi-liquid consistency, such as milks, more or less smooth creams, cream gels or pastes.

A person skilled in the art will select said active agent(s) as a function of the effect desired on the skin, the hair, the eyelashes, the eyebrows and the nails, and preferably on the skin.

The composition may also comprise at least one ingredient such as fillers with a soft-focus effect or agents for promoting the natural coloring of the skin, intended to provide an immediate visual antiaging effect.

Mention may be made especially of matt-effect agents, soft-focus fillers, fluorescers, agents for promoting the naturally pinkish coloring of the skin and abrasive or exfoliant fillers.

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect that will be relayed by the biological effect of the active agents mentioned above.

They may also, via a mechanical action (e.g.: abrasive fillers), amplify the effect of the biological active agents mentioned above.

Thus, the composition according to the invention may also comprise at least one agent chosen from additional matt-effect agents, soft-focus fillers, agents for promoting the naturally pinkish coloring of the skin, abrasive fillers or exfoliants, and mixtures thereof.

Matt-Effect Agents

The term "matt-effect agent" means agents intended to make the skin visibly more matt and less shiny.

The matting effect of the agent and/or composition containing it may especially be evaluated using a gonioreflectometer, by measuring the ratio R between the specular reflection and the scattered reflection. A value of R of less than or equal to 5 generally indicates a matting effect.

The matt-effect agent may be chosen especially from a rice starch or a corn starch: INCI name: *Zea mays* (corn) starch, such as, in particular, the product sold under the trade name Farmal CS 3650 Plus 036500 by National Starch, kaolinite, talc, a pumpkin seed extract, cellulose microbeads, plant fibers, synthetic fibers, in particular polyamide fibers, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matt-effect agents that may especially be mentioned include:
  rice or corn starch, in particular an aluminum starch octenyl succinate sold under the name Dry Flo® by the company National Starch;
  kaolinite;
  silicas;
  talc;
  a pumpkin seed extract as sold under the name Curbilene® by the company Indena;
  cellulose microbeads as described in patent application EP 1 562 562;
  fibers, such as silk fibers, cotton fibers, wool fibers, flax fibers, cellulose fibers extracted especially from wood, from vegetables or from algae, polyamide (Nylon®) fibers, modified cellulose fibers, poly-p-phenylene terephthalamide fibers, acrylic fibers, polyolefin fibers, glass fibers, silica fibers, aramid fibers, carbon fibers, Teflon® fibers, insoluble collagen fibers, polyester fibers, polyvinyl chloride or polyvinylidene chloride fibers, polyvinyl alcohol fibers, polyacrylonitrile fibers, chitosan fibers, polyurethane fibers, polyethylene phthalate fibers, fibers formed from a mixture of polymers, resorbable synthetic fibers, and mixtures thereof described in patent application EP 1 151 742;
  expanded acrylic copolymer microspheres such as those sold by the company Expancel under the name Expancel 551®;
  fillers with an optical effect as described in patent application FR 2 869 796, in particular:
  polyamide (Nylon®) powders, for instance particles of Nylon 12 such as Orgasol from Arkema with a mean size of 10 microns and a refractive index of 1.54,
  silica powders, for instance the SB150 silica beads from Miyoshi with a mean size of 5 microns and a refractive index of 1.45,
  polytetrafluoroethylene powders, for instance PTFE Ceridust 9205F from Clariant, with a mean size of 8 microns and a refractive index of 1.36,
  silicone resin powders, for instance the silicone resin Tospearl 145A from GE Silicone with a mean size of 4.5 microns and a refractive index of 1.41,
  acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku,
  wax powders, for instance the paraffin wax particles Microease 114S from Micropowders, with a mean size of 7 microns and a refractive index of 1.54,
  polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns and a refractive index of 1.48),
  elastomeric crosslinked organopolysiloxane powders coated with silicone resin, especially with silsesquioxane resin, as described, for example, U.S. Pat. No. 5,538,793. Such elastomer powders are sold under the names KSP-100, KSP-101, KSP-102, KSP-103, KSP-104 and KSP-105 by the company Shin-Etsu, and
  talc/titanium dioxide/alumina/silica composite powders, such as those sold under the name Coverleaf® AR-80 by the company Catalyst & Chemicals,
  mixtures thereof,
  compounds that absorb and/or adsorb sebum as described in patent application FR 2 869 796. Mention may be made especially of:
  silica powders, for instance the porous silica microspheres sold under the name Silica Beads SB-700 sold by the company Miyoshi, the products Sunsphere® H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass;

amorphous mixed silicate powders, especially of aluminum and magnesium, for instance the product sold under the name Neusilin UFL2 by the company Sumitomo;

polyamide (Nylon®) powders, for instance Orgasol® 4000 sold by the company Arkema, and acrylic polymer powders, especially of polymethyl methacrylate, for instance Covabead® LH85 sold by the company Wackherr; of polymethyl methacrylate/ethylene glycol dimethacrylate, for instance Dow Corning 5640 Microsponge® Skin Oil Adsorber sold by the company Dow Corning, or Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;

silicate particles, such as alumina silicate;

mixed silicate particles, such as:

magnesium aluminum silicate particles, such as saponite or hydrated magnesium aluminum silicate with a sodium sulfate sold under the trade name Sumecton® by the company Kunimine;

the magnesium silicate, hydroxyethylcellulose, black cumin oil, marrow oil and phospholipids complex or Matipure® from Lucas Meyer, and mixtures thereof.

Preferred matt-effect agents that may be used according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Soft-Focus Fillers

These fillers may be any material capable of modifying and hiding wrinkles by virtue of their intrinsic physical properties. These fillers may especially modify wrinkles via a tightening effect, a covering effect or a soft-focus effect.

The following compounds may be given as examples of fillers:

porous silica microparticles, for instance the Silica Beads® SB 150 and SB 700 from Miyoshi with a mean size of 5 μm and the series H Sunspheres® from Asahi Glass, for instance Sunspheres H33 and H51 with respective sizes of 3.5 and 5 μm;

hollow hemispherical silicone resin particles such as NLK 500®, NLK 506® and NLK 510@ from Takemoto Oil and Fat, especially described in EP-A-1 579 849;

silicone resin powders, for instance Silicon Resin Tospearl® 145 A DE GE silicone with a mean size of 4.5 μm, acrylic copolymer powders, especially of polymethyl (meth)acrylate, for instance the PMMA particles Jurymer MBI® from Nihon Junyoki, with a mean size of 8 μm, the hollow PMMA spheres sold under the name Covabead® LH85 by the company Wacker, and vinylidene/acrylonitrile/methylene methacrylate expanded microspheres sold under the name Expancel@;

wax powders, for instance the paraffin wax particles MicroEase® 114S from MicroPowders, with a mean size of 7 μm;

polyethylene powders, especially comprising at least one ethylene/acrylic acid copolymer for instance the Flobeads® EA 209 E from Sumitomo, with a mean size of 10 μm;

crosslinked elastomeric organopolysiloxane powders coated with silicone resin, especially with silsesquioxane, under the names KSP 100®, KSP101®, KSP102®, KSP103®, KSP104® and KSP105® by the company Shin-Etsu, talc/titanium dioxide/alumina/silica composite powders, for instance the Coverleaf AR-80® products from the company Catalyst & Chemicals, talc, mica, kaolin, lauryl glycine, starch powders crosslinked with octenylsuccinic anhydride, boron nitride, polytetrafluoroethylene powders, precipitated calcium carbonate, magnesium carbonate, basic magnesium carbonate, barium sulfate, hydroxyapatite, calcium silicate, cerium dioxide and glass or ceramic microcapsules, hydrophilic or hydrophobic, synthetic or natural, mineral or organic fibers such as silk fibers, cotton fibers, wool fibers, flax fibers, cellulose fibers extracted especially from wood, vegetables or algae, polyamide (Nylon®) fibers, modified cellulose fibers, poly-p-phenylene terephthalamide fibers, acrylic fibers, polyolefin fibers, glass fibers, silica fibers, aramid fibers, carbon fibers, polytetrafluoroethylene (Teflon®) fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from a mixture of polymers, resorbable synthetic fibers, and mixtures thereof described in patent application EP 1 151 742, spherical elastomeric crosslinked silicones, for instance Trefil E-505C® or E-506 C® from Dow Corning, abrasive fillers, which, via a mechanical effect, smooth out the skin microrelief, such as abrasive silica, for instance Abrasif SP® from Semanez, or nut or shell powders (for example of apricot or walnut, from Cosmetochem).

The fillers with an effect on the signs of aging are especially chosen from porous silica microparticles, hollow hemispherical silicone particles, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, basic magnesium carbonate, barium sulfate, hydroxyapatite, calcium silicate, cerium dioxide, glass or ceramic microcapsules, and silk fibers or cotton fibers, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be of any shape and in particular may be spherical or non-spherical. More preferably, these fillers are non-spherical.

The soft-focus fillers may be chosen from silica and silicate powders, especially alumina powder, powders of polymethyl methacrylate (PMMA) type, talc, silica/TiO2 or silica/zinc oxide composites, polyethylene powders, starch powders, polyamide powders, styrene/acrylic copolymer powders and silicone elastomers, and mixtures thereof.

Mention may be made in particular of talc with a number-average size of less than or equal to 3 microns, for example talc with a number-average size of 1.8 microns and especially the product sold under the trade name Talc P3® by the company Nippon Talc, Nylon® 12 powder, especially the product sold under the name Orgasol 2002 Extra D Nat Cos® by the company Atochem, silica particles 1% to 2% surface-treated with a mineral wax (INCI name: hydrated silica (and) paraffin) such as the products sold by the company Degussa, amorphous silica microspheres, such as the products sold under the name Sunsphere, for example of reference H-53® by the company Asahi Glass, and silica microbeads such as those sold under the name SB-700® or SB-150® by the company Miyoshi, this list not being limiting.

The concentration of these fillers with an effect on the signs of aging in the compositions according to the invention may be between 0.1% and 40%, or even between 0.1% and 20% by weight, relative to the total weight of the composition.

The examples that follow serve to illustrate the invention without, however, being limiting in nature. In these examples, the amounts of the composition ingredients are given as weight percentages relative to the total weight of the composition.

EXAMPLES 1 TO 3

Formulations containing the following ingredients were prepared:

|  | 1 (invention) | 2 | 3 |
|---|---|---|---|
| SODIUM POLYACRYLOYLDIMETHYL TAURATE (AND) POLYSORBATE 80 (AND) SORBITAN OLEATE (SIMULGEL 800—SEPPIC) | 2 | 2 | 2 |
| OCTOCRYLENE (UVINUL N539—BASF) | 7 | 7 | 7 |
| ARACHIDYL ALCOHOL (AND) BEHENYL ALCOHOL (AND) ARACHIDYL GLUCOSIDE (MONTANOV 202—SEPPIC) | 4 | 4 | 4 |
| HOMOSALATE | 5 | 5 | 5 |
| BUTYLMETHOXYDIBENZOYL METHANE | 3 | 3 | 3 |
| ETHYLHEXYL SALICYLATE | 5 | 5 | 5 |
| PHENOXYETHANOL | 0.5 | 0.5 | 0.5 |
| BEHENYL BEHENATE | 1 | 0 | 0 |
| POLYMETHYLENE WAX (CIREBELLE 303) | 0 | 1 | 0 |
| WATER QS | 100.0 | 100.0 | 100.0 |

For each of the compositions 1 to 3, the sun protection factor (SPF) associated therewith was then determined. This was determined by using the in vitro method described by V. Wandel et al. in SOFW Journal 127 (2001); this method consists in determining the monochromatic protection factors over a wavelength range from 290 to 400 nm and in calculating therefrom the sun protection factor according to a given mathematical equation. The measurement was taken with a 1 nm increment on a UV-1000S machine from the company Labsphere, 0.6 mg/cm² of product being spread on a frosted PMMA plate. The results (mean value corresponding to plates per product, 10 points per plate) are collated in table (I) below:

Measuring Matt Effect by In Vitro Evaluation

The matt effect obtained with composition 1 according to the invention and with compositions 2 and 3 given by way of comparative example was measured, using a contrast card (Prufkarte 24/5-250 cm² type) sold by the company Erichsen. The composition was spread in an amount of 2 mg/cm² by means of a mechanical film drawer to obtain a film 100 microns thick. The cards were stored for 24 hours at 37° C. under a controlled atmosphere at between 15% and 25% humidity. 1 spray of a mixture (20% oleic acid+80% Vichy water+1% Oleth-10) was applied; the amount deposited is about 0.3 g per spray. The reflection was measured at T0 using a gonioreflectometer (GU T0), a 6-minute waiting period at room temperature was observed and a new measurement was then taken (GU T6 min). The result obtained is the ratio R between the specular reflection and the scattered reflection (gloss units). The value of R is proportionately smaller the greater the matt effect.

Table (I) below gives values for the immediate gloss units (GU T0) and after spraying on an artificial sebum/sweat solution (GU T6 min).

TABLE I

|  | Immediate matt effect T0 | Matt effect after spraying with artificial sebum/sweat solution T6 min | in vitro SPF |
|---|---|---|---|
| Base SPF + 1% behenyl behenate (Ex. 1) | 2.8 | 3.55 | 22.5 |
| Base SPF + 1% cirebelle 303 (Ex. 2) | 3.25 | 11.45 | 15.38 |
| Base SPF (Ex. 3) | 3.23 | 9.6 | 14.3 |

EXAMPLES 4 TO 6

The following three compositions were prepared:

|  | 4 | 5 | 6 |
|---|---|---|---|
| Arachidyl alcohol (and) behenyl alcohol (and) arachidyl glucoside (Montanov 202—SEPPIC) | 3 | 3 | 3 |
| Octocrylene | 7 | 7 | 7 |
| Fragrance | 0.1 | 0.1 | 0.1 |
| Disodium EDTA | 0.1 | 0.1 | 0.1 |
| Butylmethoxydibenzoylmethane | 3 | 3 | 3 |
| Silica (and) titanium dioxide | 3 | 3 | 3 |
| Paraffin | 0.5 | 0.5 | 0.5 |
| Isononyl isononanoate | 2.5 | 2.5 | 2.5 |
| Phenoxyethanol | 0.5 | 0.5 | 0.5 |
| Dimethicone | 3 | 3 | 3 |
| Glycerol | 5 | 5 | 5 |
| Behenyl behenate | 0.5 | 1 | 0 |
| Ammonium acryloyldimethyltaurate/VP copolymer (Aristoflex AVC—Clariant) | 0.5 | 0.5 | 0.5 |
| Dicaprylyl carbonate | 5 | 5 | 5 |
| Water qs | 66.3 | 66.3 | 66.3 |

The SPF of compositions 4, 5 and 6 was measured in vivo according to the method ISO 24444 (2010).

The SPF of the compositions according to the invention comprising behenyl behenate is markedly greater than that of the composition not containing any.

| | in vivo SPF |
|---|---|
| Base SPF 2 (Ex 6) comparative | 12 |
| Base SPF 2 + 0.5% behenyl behenate (Ex. 4) Invention | 16 |
| Base SPF 2 + 1% behenyl behenate (Ex. 5) Invention | 19 |

The invention claimed is:

1. A composition which comprises, in a cosmetically acceptable medium:
    (a) 5% to 25% by weight relative to the total weight of the composition of at least one photoprotective system capable of screening out UV radiation and which comprises one or more lipophilic organic screening agents;
    (b) from 0.5% to 3% by weight relative to the total weight of the composition of at least one carboxylic acid ester chosen from behenyl behenate and arachidyl arachidate; and
    (c) 0.01% to 10% by weight relative to the total weight of the composition of at least one $C_8$-$C_{30}$alkyl(poly)glycoside,
    and wherein the composition has an increased matt effect.

2. The composition as claimed in claim 1, in which the at least one carboxylic acid ester is behenyl behenate.

3. The composition as claimed in claim 1, in which the at least one $C_8$-$C_{30}$alkyl(poly)glycoside is chosen from cocoyl (poly)glucoside, arachidyl(poly)glucoside, myristyl(poly)glucoside, eetylstearyl(poly)glucoside, $C_{12}$-$C_{20}$alkyl(poly)glucosides, isostearyl(poly)glucoside and octyldodecyl (poly)xyloside.

4. The composition as claimed in claim 1, in which the at least one $C_8$-$C_{30}$alkyl(poly)glycoside is present in concentrations ranging from 0.1% to 6% by weight relative to the total weight of the composition.

5. The composition as claimed in claim 1, also comprising at least one C8-40 fatty alcohol in a concentration ranging from 0.01% to 15% by weight relative to the total weight of the composition.

6. The composition as claimed in claim 5, in which the at least one fatty alcohol is present in concentrations ranging from 0.1% to 10% by weight relative to the total weight of the composition.

7. The composition as claimed in claim 1, in which the one or more lipophilic organic UV-screening agents are chosen from cinnamic derivatives; anthranilates; salicylic derivatives; dibenzoylmethane derivatives; camphor derivatives; benzophenone derivatives; β, β-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; a-alkylstyrene-based dimers; 4,4-diarylbutadienes; merocyanin derivatives; and mixtures thereof.

8. The composition as claimed in claim 1, in which the photoprotective system is formed from one or more lipophilic organic UV-screening agents chosen from:
    Ethylhexyl methoxycinnamate,
    Ethylhexyl salicylate,
    Homosalate,
    Butylmethoxydibenzoylmethane,
    Octocrylene,
    Phenylbenzimidazolesulfonic acid,
    Benzophenone-3,
    Benzophenone-4,
    Benzophenone-5,
    n-Hexyl 2-(4-diethylamino-2-hydroxybenzoyl)benzoate,
    4-Methylbenzylidenecamphor,
    Terephthalylidenedicamphorsulfonic acid,
    Disodium phenyldibenzimidazoletetrasulfonate,
    Methylenebis(benzotriazolyl)tetramethylbutylphenol,
    Bis(ethylhexyloxyphenol)methoxyphenyltriazine,
    Ethylhexyl triazone,
    Diethylhexyl butamidotriazone,
    2,4,6-Tris(dineopentyl 4'-aminobenzalmalonate)-s-triazine,
    2,4,6-Tris(diisobutyl 4'-aminobenzalmalonate)-s-triazine,
    2,4-Bis(dineopentyl 4'-aminobenzalmalonate)-6-(n-butyl 4'-aminobenzoate)-s-triazine,
    2,4,6-Tris(biphenyl-4-yl)-1,3,5-triazine,
    2,4,6-Tris(terphenyl)-1,3,5-triazine,
    Drometrizole trisiloxane,
    Polysilicone-15,
    1,1-Dicarboxy(2,2'-dimethylpropyl)-4,4-diphenylbutadiene;
    2,4-Bis[5-(1-dimethylpropyl)benzoxazol-2-yl-(4-phenyl)imino]-6-(2-ethylhexyl)imino-1,3,5-triazine,
    and mixtures thereof.

9. The composition as claimed in claim 1, which further comprises one or more mineral UV-screening agents that are coated or uncoated metal oxide pigments.

10. The composition as defined in claim 1 wherein the medium is a cosmetically acceptable medium and wherein the at least one carboxylic acid ester increases the sun protection factor (SPF) of the composition.

11. A cosmetic process for caring for and/or making up a keratin material, comprising the application, to the surface of said keratin material, of a composition as defined in claim 1.

12. A cosmetic process for limiting darkening of the skin and/or improving the color and/or uniformity of the complexion, comprising the application, to the surface of the keratin material, of a composition as defined in claim 1.

13. A cosmetic process for preventing and/or treating the signs of aging of a keratin material, comprising the application, to the surface of the keratin material, of a composition as defined in claim 1.

14. The composition as claimed in claim 1, in which the at least one carboxylic acid ester is arachidyl arachidate.

15. The composition as claimed in claim 1, wherein the at least one carboxylic acid ester comprises behenyl behenate and the at least one $C_8$-$C_{30}$alkyl(poly)glycoside comprises arachidyl(poly)glucoside.

* * * * *